(12) United States Patent
Esses

(10) Patent No.: US 9,931,424 B2
(45) Date of Patent: Apr. 3, 2018

(54) POSITIONABLE AIR FRESHENER

(71) Applicant: Alfred Esses, Brooklyn, NY (US)

(72) Inventor: Alfred Esses, Brooklyn, NY (US)

(73) Assignee: Alfred Esses, Brooklyn, NY (US)

( * ) Notice: Subject to any disclaimer, the term of this patent is extended or adjusted under 35 U.S.C. 154(b) by 0 days.

(21) Appl. No.: 15/155,659

(22) Filed: May 16, 2016

(65) Prior Publication Data

US 2016/0256585 A1 Sep. 8, 2016

Related U.S. Application Data

(63) Continuation-in-part of application No. 14/341,382, filed on Jul. 25, 2014, now Pat. No. 9,408,936.

(51) Int. Cl.

| | |
|---|---|
| *A61L 9/00* | (2006.01) |
| *A62B 7/08* | (2006.01) |
| *A01G 13/06* | (2006.01) |
| *A61M 16/00* | (2006.01) |
| *A61L 9/03* | (2006.01) |
| *H05B 1/02* | (2006.01) |
| *H05B 3/03* | (2006.01) |

(52) U.S. Cl.
CPC .............. *A61L 9/03* (2013.01); *H05B 1/0297* (2013.01); *H05B 3/03* (2013.01); *A61L 2209/133* (2013.01); *A61L 2209/134* (2013.01); *A61L 2209/15* (2013.01)

(58) Field of Classification Search
CPC .............. A61L 9/00; A61L 9/03; A61L 9/037
USPC ........ 422/1, 5, 123, 125, 306; 392/386, 391, 392/394
See application file for complete search history.

(56) References Cited

U.S. PATENT DOCUMENTS 3,872,280 A * 3/1975 Van Dalen ................ A61L 9/03
128/203.27

* cited by examiner

*Primary Examiner* — Monzer R Chorbaji
(74) *Attorney, Agent, or Firm* — Moritt Hock & Hamroff LLP; Steven S. Rubin, Esq.

(57) ABSTRACT

Technologies are generally described for positionable air freshener devices. The devices may comprise an insertion section. The insertion section may include electrodes effective to receive and conduct an electric current and secure the device to an electric source. The insertion section may include a ball. The devices may comprise a base. The base may include a socket. The socket may attach to the ball. The socket and ball may form a ball joint. The base may include a port effective to receive electric current from the electrodes. The base may include a collar effective to apply heat sufficient to release a fragrance from a material when electrical current is supplied to the collar from the electrodes. The device may include a cap with a ring shaped cross-section, sized and shaped so as to be connectable to the base such that the port is accessible when the cap is connected.

20 Claims, 6 Drawing Sheets

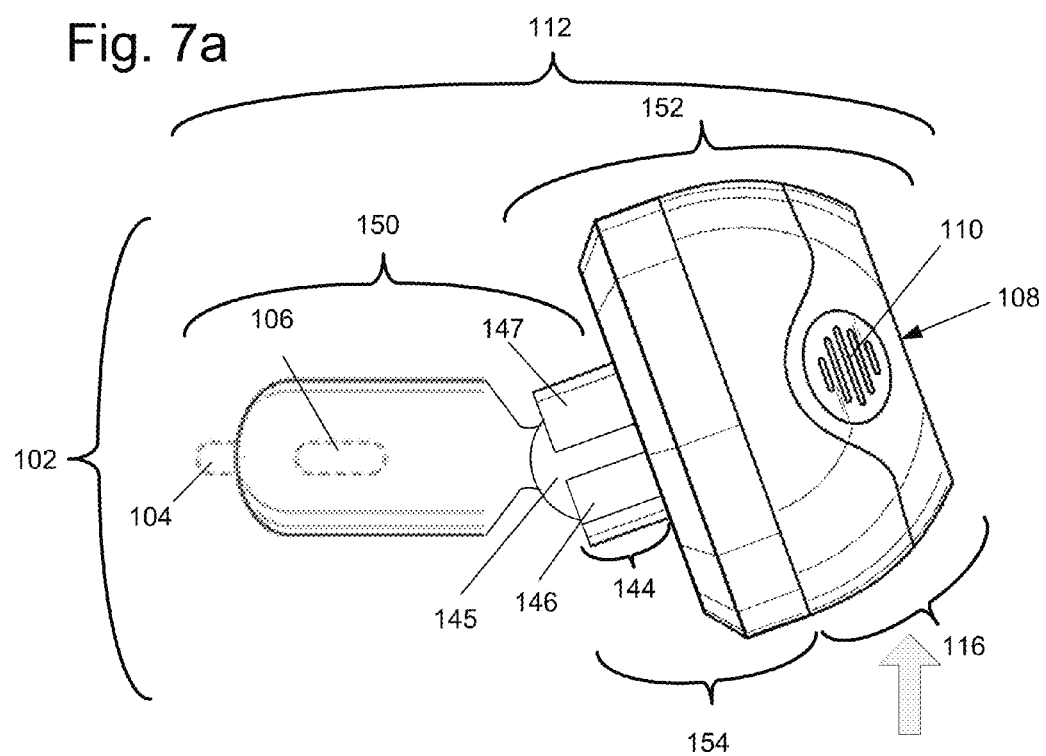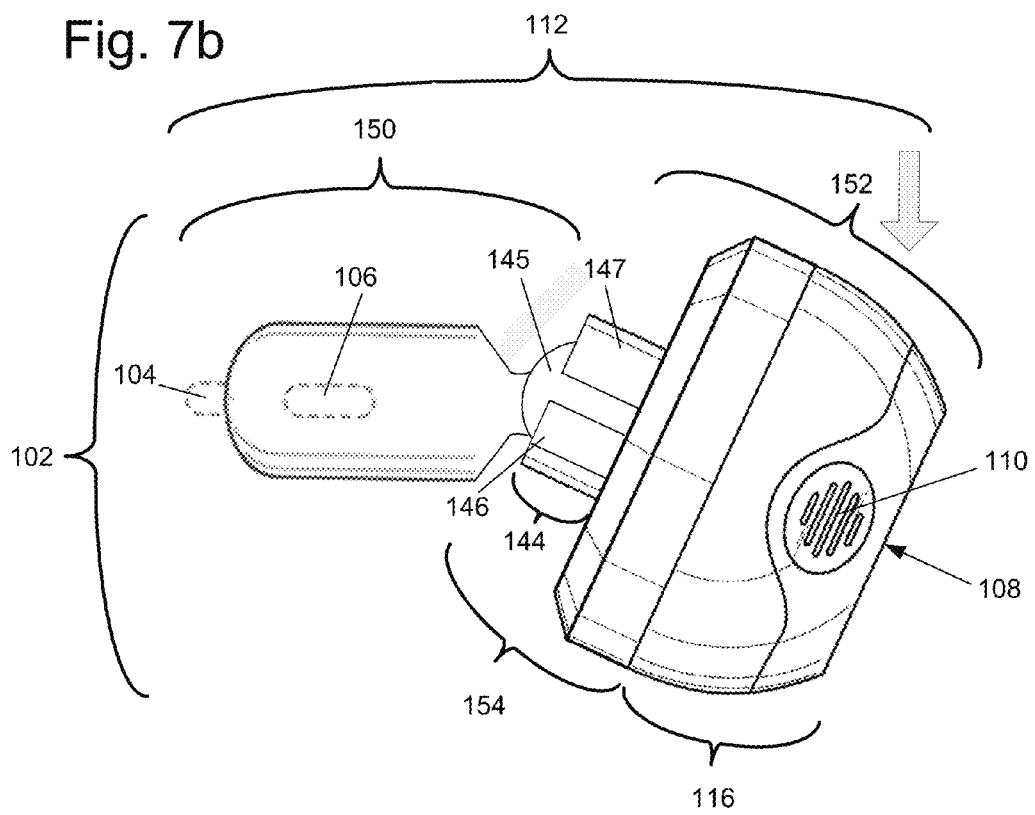

POSITIONABLE AIR FRESHENER

CROSS-REFERENCE TO RELATED APPLICATIONS

The present application is a Continuation-In-Part application that claims priority under 35 U.S.C. § 120 to U.S. application Ser. No. 14/341,382 entitled "Air Freshener" filed on Jul. 25, 2014, the entirety of which is incorporated herein by reference.

BACKGROUND

Air fresheners reduce or mask undesired odors and emit pleasant odors. Air fresheners typically emit a pleasant odor in the form of a fragrance. Air fresheners include sprays, candles, oils, gels, and plug-ins.

SUMMARY OF THE INVENTION

In one example, positionable air freshener devices are generally described. The devices may comprise an insertion section. The insertion section may include electrodes on a first side. The electrodes may be effective to receive and conduct an electric current. The electrodes may be further effective to secure the device to an electric source at the first side of the insertion section. The insertion section may include a ball at a second side. The devices may include a base. The base may include a socket at a first end. The socket may attach to the ball on the second end of the insertion section. The socket and ball may form a ball joint. The base may include a port at a second end of the base. The port may be effective to receive at least part of the electric current from the electrodes. The base may include a collar. The collar may be within the base. The collar may be positioned between the first end of the base and the second end of the base. The collar may be effective to apply heat sufficient to release a fragrance from a material infused with the fragrance when at least part of the electrical current is supplied to the collar from the electrodes. The devices may include a cap. The cap may have a ring shaped cross-section. The cap may be sized and shaped so as to be connectable to the base around the second end of the base such that the port is accessible when the cap is connected to the base.

In another example, methods for assembling a device are generally described. The methods may comprise positioning a base with respect to an insertion section. The base may include a port at the first end of the base. A second end of the base may include a socket. The socket may be attached to a ball on a first side of the insertion section. The socket and ball may form a ball joint. The methods may comprise attaching a cap to a first end of a base. The cap may have a ring shaped cross section. The cap may be effective to secure a material infused with a fragrance to a collar and the base. The collar may be positioned between the first end of the base and the second end of the base. The insertion section may include electrodes effective to receive and conduct an electric current. The electrodes may be further effective to secure the device to an electric source such that a second side of the insertion section is proximate to the electric source. The port may be effective to receive at least part of the electric current from the electrodes. The collar may be effective to apply heat sufficient to release the fragrance from the material infused with the fragrance when at least part of the electrical current is supplied to the collar from the electrodes.

In another example, methods for releasing fragrance from a material are generally described. The methods may comprise placing a material infused with a fragrance around a collar. The collar may be positioned between a first end of a base and a second end of the base. The first end of the base may include a socket. The socket may be attached to a ball on a first side of an insertion section. The socket and ball may form a ball joint. The insertion section may include electrodes effective to receive and conduct an electric current. The electrodes may be further effective to secure a device to an electric source at a second side of the insertion section. The methods may comprise attaching a cap to the second end of the base. The cap may have a ring shaped cross section. The cap may be effective to secure the material infused with the fragrance to the collar and the base. The methods may comprise attaching the electrodes to the electric source. The methods may comprise adjusting the position of the base with respect to the insertion section. The methods may comprise receiving the electric current from the electrodes at the collar. The collar may be effective to apply heat sufficient to release the fragrance from the material infused with the fragrance.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims taken in conjunction with the accompanying drawings. Understanding that these drawings depict only some embodiments in accordance with the disclosure and are therefore not to be considered limiting of its scope, the disclosure will be described with additional specificity and detail by reference to the accompanying drawings in which:

FIG. 7a is a side view of an air freshener with the positionable outer section positioned upward;

FIG. 7b is a side view of an air freshener with the positionable outer section positioned downward;

Figure 1:
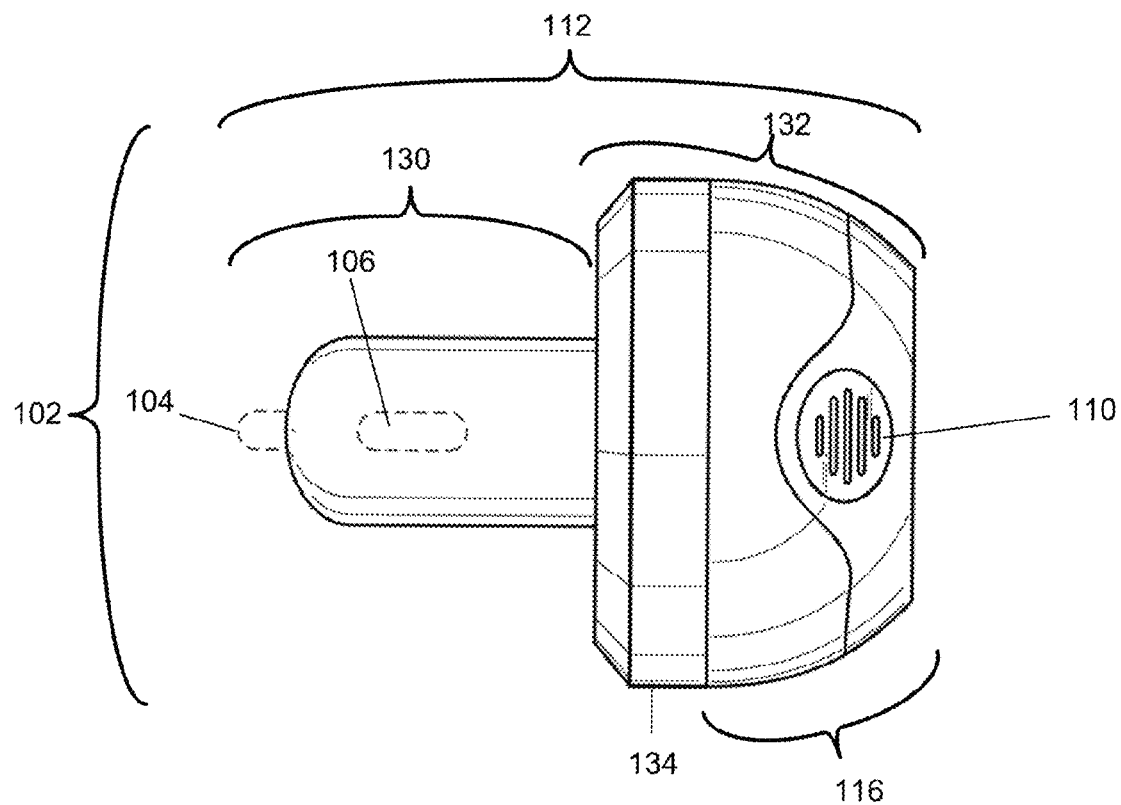
FIG. 1 is a side view of an air freshener.

all in accordance with an embodiment of the invention.

DETAILED DESCRIPTION

In the following detailed description, reference is made to the accompanying drawings which form a part thereof. In the drawings, similar symbols typically identify similar components unless context indicates otherwise. The illustrative embodiments described in the detailed description, drawings and claims are not meant to be limiting. Other embodiments may be utilized and other changes may be made without departing from the spirit or scope of the subject matter presented herein. It will be readily understood that the aspects of the present disclosure as generally described herein and as illustrated in the accompanying figures can be arranged, substituted, combined, separated and/or designed in a wide variety of different configurations all of which are explicitly contemplated herein.

FIG. 1 is a side view of an air freshener in accordance with an embodiment of the invention. An air freshener 102 may include a body 112 comprising an insertion section 130 connected to an outer section 132. Insertion section 130 of body 112 may have a cylindrical shape and may have a first and a second end. Insertion section 130 may include an anode electrode 104 extending axially from the first end. The second end of insertion section 130 may be connected to outer section 132. Insertion section 130 may include cathode electrodes 106 extending radially from the sides of insertion section 130. Insertion section 130 including anode electrode 104 and cathode electrodes 106, may be arranged such that air freshener 102 may be plugged into a cigarette lighter socket, such as a vehicle cigarette lighter socket, with the anode electrode 104 and the cathode electrodes 106 aligning and connecting to the electrodes of the vehicle cigarette lighter socket respectively. The current provided by the vehicle cigarette lighter socket may be direct current and may be 12 volts.

Outer section 132 may be substantially hemispherical shaped and include a cap 116 and a base 134. Outer section 132 may be connected to insertion section 130 axially at base 134. Base 134 may be substantially cylindrically shaped with a substantially larger radius than insertion section 130. Base 134 may have a first and a second side and may include flat edges, textured edges or be smooth. Base 134 may slightly taper in radius axially on the first side of base 134. The first side of base 134 may be attached to the second side of insertion section 130. Cap 116 may extend axially from base 134 on the second side of base 134. Cap 116 may be substantially hemispherical in shape and may be smooth and taper in radius along an axial direction away from base 134. Cap 116 may have a ring shaped cross-section defining an opening in the middle of cap 116 where the second end of base 134 may be exposed when cap 116 is connected to base 134. Cap 116 may include vents 110. Vents 110 may be grilled, slotted, screened, or any other venting configuration capable of allowing air to flow between inside of cap 116 and outside of cap 116.

Figure 2:
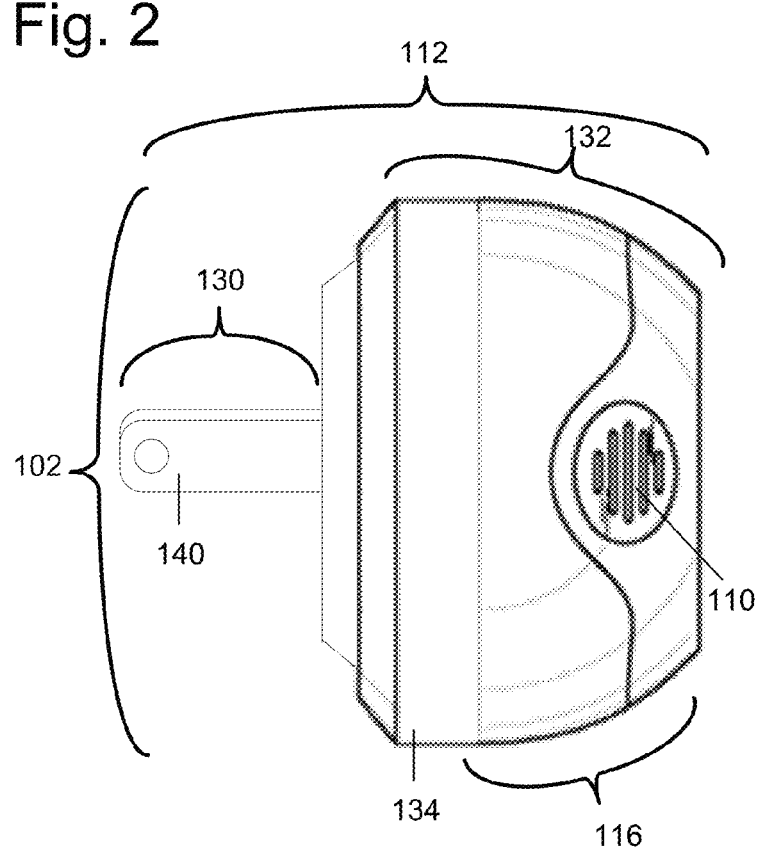
FIG. 2 is a side view of an air freshener with metal terminals.

FIG. 2 is a side view of air freshener 102 with metal terminals in accordance with an embodiment of the invention. Those components in FIG. 2 that are labeled identically to components of FIG. 1 will not be described again for the purposes of clarity. In another embodiment, insertion section 130 may include electrodes 140 that are metal prongs or terminals extending axially from base 134. Metal terminals 140 may be arranged such that air freshener 102 may be plugged into an electrical socket. Metal terminals 140 may secure air freshener 102 to an electric socket when plugged into the electric socket. An electrical current may be provided to metal terminals 140 and subsequently to air freshener 102 when metal terminals 140 are plugged into an electrical socket.

Figure 3:
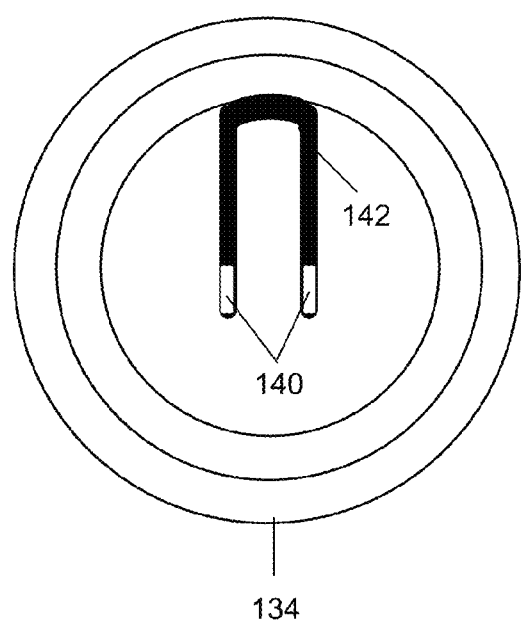
FIG. 3 is a rear view of an air freshener with metal terminals.

FIG. 3 is a rear view of air freshener 102 with metal terminals in accordance with an embodiment of the invention. Those components in FIG. 3 that are labeled identically to components of FIG. 1-2 will not be described again for the purpose of clarity. Metal terminals 140 in insertion section 130 may be retractable. Metal terminals 140 may be able to fold 90 degrees to range from perpendicular to the surface of the first side of base 134 to parallel to the surface of the first side of base 134. Grooves 142 may be present in the surface of base 134 such that metal terminals 140, when folded parallel to the surface of the first side of base 134, may recess into the surface of the first side of base 134. When recessed into the surface of the first side of base 134, metal terminals 140 may be completely submerged within the first side of base 134.

Figure 4:
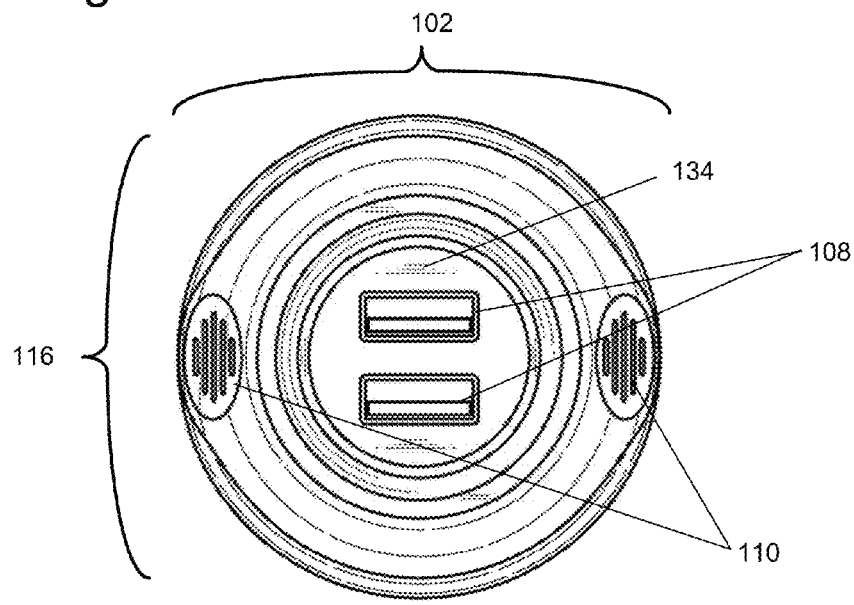
FIG. 4 is a front view illustrating two ports of an air freshener.

FIG. 4 is a front view illustrating two ports of air freshener 102 in accordance with an embodiment of the invention. Those components in FIG. 4 that are labeled identically to components of FIG. 1-3 will not be described again for the purposes of clarity. Air freshener 102 may include ports 108 and grilled vents 110. Ports 108 may be included in the second side of base 134 and grilled vents 110 may be included in cap 116. Ports 108 may be universal serial bus (USB) ports and may be accessible when cap 116 is attached to base 134. Cap 116 may have a ring shaped cross-section and may be sized and shaped so as to be connectable to base 134 around the second end of base 134 such that ports 108 are accessible when cap 116 is connected. In one embodiment, ports 108 may be powered by an electric current from anode electrode 104 and cathode electrode 106 (illustrated in FIG. 1) when connected to vehicle cigarette lighter socket electrodes. In another embodiment, ports may be powered by an electric current from metal terminals 140 (illustrated in FIG. 2-3) when plugged into an electric socket. As described in more detail below, vents 110 in cap 116 may allow fragrance to flow from air freshener 102.

Figure 5:
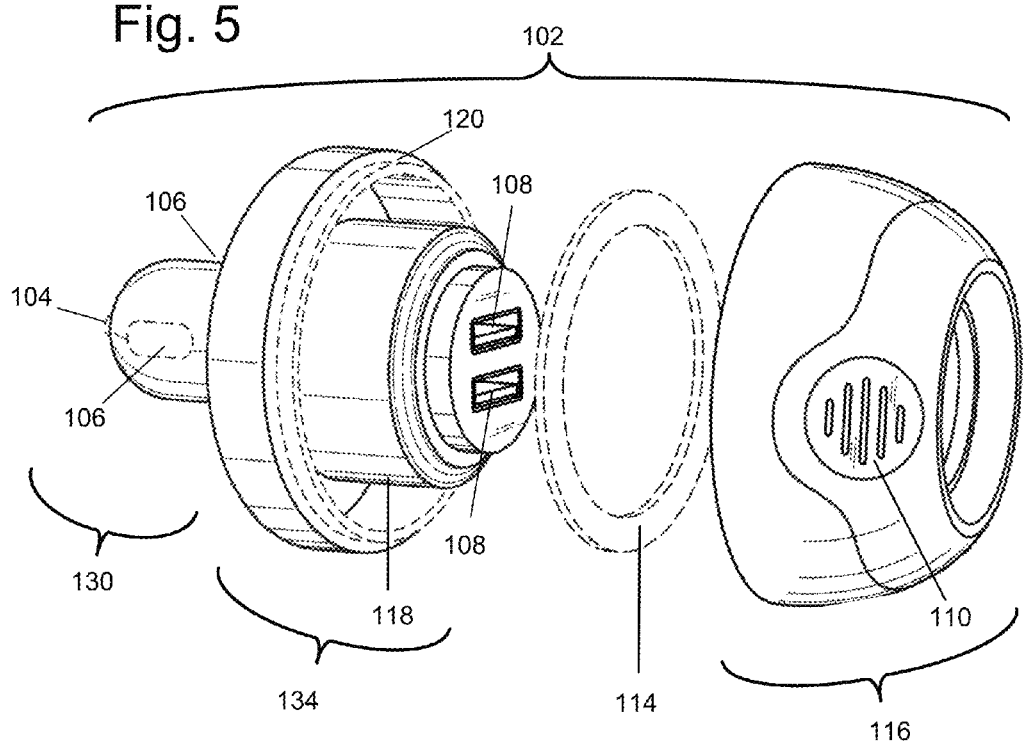
FIG. 5 is an angled side perspective view illustrating a body, a disk, and a cap enclosure of an air freshener.

FIG. 5 is an angled side perspective view illustrating a body, a disk, and a cap enclosure of car air freshener 102 in accordance with an embodiment of the invention. Those components in FIG. 5 that are labeled identically to components of FIG. 1-4 will not be described again for the purposes of clarity. Air freshener 102 may include insertion section 130, base 134, a disk 114 and cap 116. Insertion section 130 may include anode electrode 104 and cathode electrodes 106, and may be attached to base 134. Base 134 may include USB ports 108, and collar 118. Current provided by a vehicle cigarette lighter socket may travel from electrode cathode 106 to electrode anode 104 and provide power to USB ports 108.

Disk 114 may be a liquid oil, gel or solid material infused with a fragrance. Fragrances may be any desirable fragrance including fruit scents, new car smell, etc. Disk 114 may be in the shape of a flat ring and may fit around collar 118. Collar 118 may be heated when a current provided by vehicle cigarette lighter socket travels from electrode cathode 106 to electrode anode 104. Heating of collar 118 by electric current provided by vehicle cigarette lighter socket may release fragrance from disk 114.

Cap 116 may secure disk 114 to collar 118 and base 134 when cap 116 is attached to base 134. Cap 116 may attach to base 134 and be secured to base 134 by locking mechanism 120. Locking mechanism 120 may secure cap 116 to base 134 such as by protrusions from base 134 that cap 116 may snap onto to secure to base 134. Locking mechanism 120 may secure cap 116 to base 134 such as by threads on base 134 for cap 116 to screw onto to secure to base 134. Fragrance emitted from heating of disk 114 may disperse through vents 110 in cap 116 to freshen air proximate to air freshener 102.

For example, insertion section 130 may be placed into a vehicle cigarette lighter socket such that anode electrode 104 and cathode electrodes 106 align with electrodes in vehicle cigarette lighter socket. Electric current may travel from vehicle cigarette lighter socket to cathode electrodes 106 through air freshener 102 circuitry to anode electrode 104 and back to vehicle cigarette lighter socket. Electric current may be direct current and may be 12 volts. Air freshener 102 circuitry may be configured to supply electric current to USB ports 108. USB ports 108 may function to supply power to connected USB cables for powering and/or charging devices attached to a connected USB cable. Air freshener 102 circuitry may further be configured to provide electric current to heat collar 118 in base 134. Collar 118 may be heated by electric current as current travels from cathode electrodes 106 to anode electrode 106. Collar 118, heated by electric current, may conduct heat to disk 114 located and secured around collar 118 by cap 116. Heating of disk 114 may release fragrance infused within material of disk 114. Released fragrance may diffuse into the air. Air with diffused fragrance may disperse through vents 110 and provide fragrance to air proximate to air freshener 102.

Figure 6:
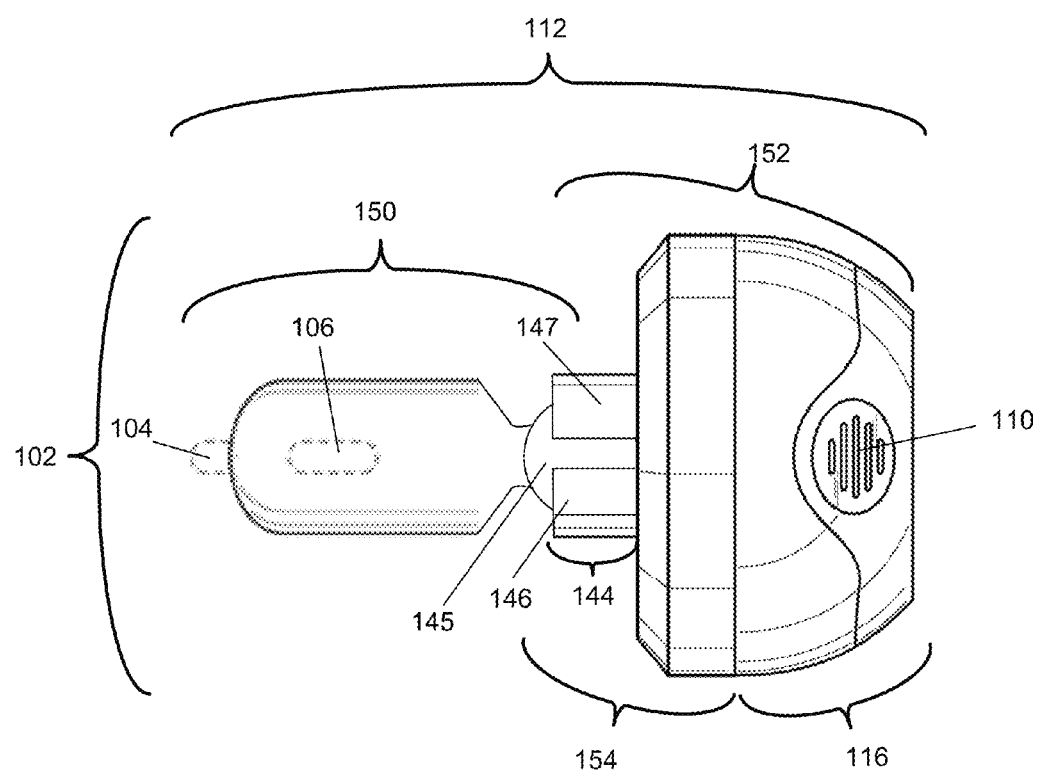
FIG. 6 is a side view of an air freshener with a positionable outer section.

FIG. 6 is a side view of an air freshener with a positionable outer section 152 in accordance with an embodiment of the invention. Those components in FIG. 6 that are labeled identically to components of FIG. 1-5 will not be described again for the purposes of clarity.

Air freshener 102 may include insertion section 150 and outer section 152. Outer section 152 may include base 154. Base 154 may include a socket 144 on a first side of base 154, opposite to second side of base 154 attached to cap 116. Socket 144 may include tabs 146, 147 extending perpendicularly away from first side of base 154. Socket 144 may attach to, and secure, a ball 145 to form a ball joint. Socket 144 securing ball 145 may allow ball 145 to pivot within socket 144.

Insertion section 150 may include ball 145 on the second side of insertion section 150, opposite first side of insertion section 150 including anode electrode 104. Insertion section 150 may be attached to outer section 152 axially. Ball 145 of insertion section 150 may be secured within socket 144 of outer section 152 to form a ball joint. As shown in more detail below, ball of insertion section 150 attached to socket 144 of outer section 152 may allow outer section 152 to be positionable with respect to insertion section 150.

FIG. 7a is a side view of an air freshener with a positionable outer section 152 positioned upward in accordance with an embodiment of the invention. FIG. 7b is a side view of an air freshener with a positionable outer section 152 positioned downward in accordance with an embodiment of the invention. Those components in FIGS. 7a and 7b that are labeled identically to components of FIG. 1-6 will not be described again for the purposes of clarity.

As shown in FIG. 7a, ball 145 of insertion section 150 may be secured within socket 144 of outer section 152 and connect insertion section 150 to outer section 152 axially. Outer section 152 may be positioned upward with respect to insertion section 150 by pivoting socket 144 upward on ball 145. Insertion section 150 may also be considered to be positioned upward with respect to outer section 152 in FIG. 7a. As shown in FIG. 7b, outer section 152 may be positioned downward with respect to insertion section 150 by pivoting socket 144 downward on ball 145. Insertion section 150 may also be considered to be positioned downward with respect to outer section 152 in FIG. 7b. Outer section 152 may be positioned to the left or to the right with respect to insertion section 150. Insertion section 150 may be positioned to the left or to the right with respect to outer section 152.

Insertion section 150 may be positioned any combination of up, down left or right with respect to outer section 152.

Outer section 152 may be positioned any combination of up, down, left or right with respect to insertion section 150.

For example, insertion section 150 of air freshener 102 may be inserted into a vehicle cigarette lighter socket. Insertion section 150 may be fixed within the vehicle cigarette lighter socket. Outer section 152 may be able to pivot on ball 145 to adjust a position of outer section 152. Outer section 152 may be able to tilt upwards, downwards, or left or right with respect to insertion section 150. Outer section 152 may be positioned so as to increase accessibility to ports 108 or cap 116.

Figure 8:
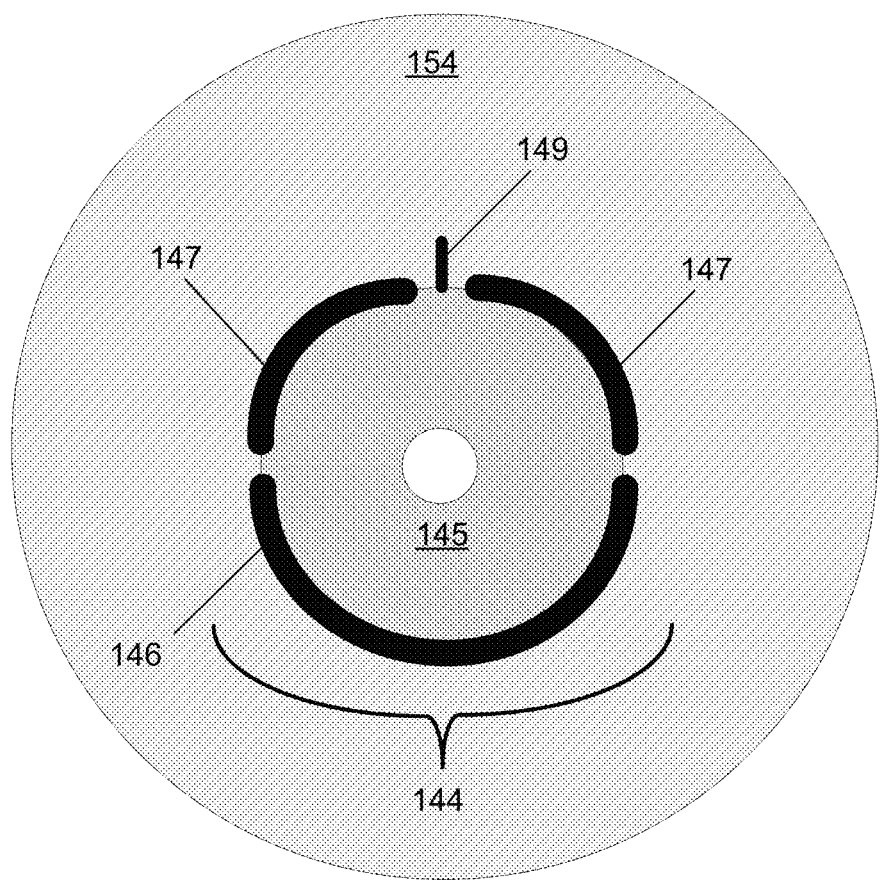
FIG. 8 is a rear view of a ball of an insertion section secured in a socket of the positionable outer section.

FIG. 8 is a rear view of ball 145 of insertion section 150 secured in socket 144 of positionable outer section 152 in accordance with an embodiment of the invention. Those components in FIG. 8 that are labeled identically to components of FIG. 1-7 will not be described again for the purposes of clarity.

Socket 144 may include tabs 146, 147. Tabs 146, 147 may extend perpendicularly away from a first end of base 154. Tab 146 may substantially enclose a lower half of ball 145. Tabs 147 may each substantially enclose an upper quarter of ball 145. Tab 146 and tabs 147 may comprise socket 144. Together, tab 146 and tabs 147 may substantially enclose ball 145 and secure ball within socket 144. Ball 145 may include a prong 149, positioned between tabs 147. Prong 149 may prevent ball 145 from rotating axially with respect to socket 144 and damaging components within air freshener 102.

Among other potential benefits, a device in accordance with the disclosure may provide a desired fragrance within a vehicle while also providing operational USB ports for use. Vehicles with a single cigarette lighter socket may be able to utilize the single socket for more than one purpose. Multiple devices, such as global positioning devices (GPS), cell phone chargers, media players, etc., may be attached to the USB ports while freshening the air of the vehicle. A device in accordance with the disclosure may be positionable so as to be more functional when inserted into a cigarette lighter socket that may not be easily accessed by a fixed device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
an insertion section, wherein the insertion section includes:
electrodes wherein the electrodes are on a first side of the insertion section, the electrodes are effective to receive and conduct an electric current and the electrodes are further effective to secure the device to an electric source at the first side of the insertion section; and
a ball at a second side of the insertion section;
a base, a first end of the base including a socket, wherein the socket attaches to the ball on the second end of the insertion section, the socket and ball forming a ball joint, the base includes:
a port at a second end of the base, the port effective to receive at least part of the electric current from the electrodes and supply power to an additional device attached to the port;
a collar within the base, positioned between the first end of the base and the second end of the base, wherein the collar is effective to apply heat sufficient to release a fragrance from a material infused with the fragrance when at least part of the electrical current is supplied to the collar from the electrodes; and a cap, where the cap has a ring shaped cross-section and is sized and shaped so as to be connectable to the base around the second end of the base such that the port is accessible when the cap is connected to the base.

2. The device of claim 1, wherein the electrodes are configured to align and connect to electrodes of a vehicle cigarette lighter socket.

3. The device of claim 1, wherein the base is positionable with respect to the insertion section.

4. The device of claim 1, wherein the socket includes tabs that extend perpendicularly away from the first end of the base.

5. The device of claim 4, wherein the ball includes a prong positioned between the tabs and prevents the ball from rotating axially with respect to the socket.

6. The device of claim 1, wherein the cap includes a vent effective to disperse the fragrance.

7. The device of claim 1, wherein the material infused with the fragrance includes a liquid oil, a gel, or a solid and the material is in the shape of a flat ring.

8. The device of claim 1, wherein:
the base includes threads on the second side of the base; and
the cap is effective to be screwed onto the threads so that the cap is secured to the base.

9. The device of claim 1, wherein:
the electrodes are configured to align and connect to electrodes of a vehicle cigarette lighter socket;
the material infused with the fragrance is a solid in the shape of a flat ring; and
the cap includes a vent effective to disperse the fragrance.

10. A method for assembling a device, the method comprising:
positioning a base with respect to an insertion section, wherein:
the base includes a port at the first end of the base and a second end of the base includes a socket, the socket being attached to a ball on a first side of the insertion section, the socket and ball forming a ball joint; and
attaching a cap to a first end of the base, the cap having a ring shaped cross section and effective to secure a material infused with a fragrance to a collar and the base, wherein:
the collar is positioned between the first end of the base and the second end of the base;
the insertion section includes electrodes effective to receive and conduct an electric current and the electrodes are further effective to secure the device to an electric source at a second side of the insertion section;
the port effective to receive at least part of the electric current from the electrodes and supply power to an additional device attached to the port; and
the collar effective to apply heat sufficient to release the fragrance from the material infused with the fragrance when at least part of the electrical current is supplied to the collar from the electrodes.

11. The method of claim 10, wherein the electrodes are configured to align and connect to electrodes of a vehicle cigarette lighter socket, the method further comprising inserting the second side of the insertion section into a vehicle cigarette lighter socket.

12. The method of claim 10, wherein the base is positionable up, down, left, or right with respect to the insertion section.

13. The method of claim 10, wherein the socket includes tabs that extend perpendicularly away from the first end of the base.

14. The method of claim 13, wherein the ball includes a prong positioned between the tabs and prevents the ball from rotating axially with respect to the socket.

15. The method of claim 10, wherein the material infused with the fragrance includes a liquid oil, a gel, or a solid and the material is in the shape of a flat ring.

16. The method of claim 10, wherein the cap includes a vent effective to disperse the fragrance.

17. The method of claim 10, further comprising attaching the cap to the first end of the base with a locking mechanism, wherein the locking mechanism includes threads on the first end of the base and the cap screws onto the threads to secure the cap to the base.

18. The method of claim 10, wherein:
the electrodes are configured to align and connect to the electrodes of a vehicle cigarette lighter socket;
the material infused with the fragrance is a solid in the shape of a flat ring; and
the cap includes a vent effective to disperse the fragrance.

19. The method of claim 10, wherein the electrodes are configured to align and connect to the electrodes of a vehicle cigarette lighter socket, the method further comprising adjusting a position of the base with respect to the insertion section.

20. A method for releasing fragrance from a material, the method comprising:
placing a material infused with a fragrance around a collar positioned between a first end of a base and a second end of the base, the first end of the base including a socket, the socket being attached to a ball on a first side of an insertion section, the socket and ball forming a ball joint, the insertion section including electrodes effective to receive and conduct an electric current and further effective to secure the insertion section to an electric source at a second side of the insertion section;
attaching a cap to the second end of the base, the cap having a ring shaped cross section and effective to secure the material infused with the fragrance to the collar and the base;
attaching the electrodes to the electric source;
adjusting the position of the base with respect to the insertion section;
receiving a first portion of the electric current from the electrodes at the collar wherein the collar is effective to apply heat sufficient to release the fragrance from the material infused with the fragrance; and
receiving a second portion of the electric current from the electrodes at a port wherein the port is effective to supply power to a device attached to the port.

* * * * *